United States Patent
Chaudhari et al.

(10) Patent No.: US 7,411,099 B2
(45) Date of Patent: *Aug. 12, 2008

(54) PROCESS FOR THE LIQUID PHASE OXIDATION OF TOLUENE TO BENZALDEHYDE

(75) Inventors: Raghunath Vitthal Chaudhari, Maharashtra (IN); Kalpendra Baburao Rajurkar, Maharashtra (IN); Sunil Sopana Tonde, Maharashtra (IN); Vilas Hari Rane, Maharashtra (IN)

(73) Assignee: Council of Scientific & Industrial Research, New Dehli (IN)

( * ) Notice: Subject to any disclaimer, the term of this patent is extended or adjusted under 35 U.S.C. 154(b) by 0 days.

This patent is subject to a terminal disclaimer.

(21) Appl. No.: 11/533,549

(22) Filed: Sep. 20, 2006

(65) Prior Publication Data
US 2007/0213566 A1   Sep. 13, 2007

(30) Foreign Application Priority Data
Mar. 10, 2006   (IN) .......................... 653/DEL/2006

(51) Int. Cl.
*C07C 45/36* (2006.01)

(52) U.S. Cl. ...................................... 568/431; 568/437

(58) Field of Classification Search ................. 568/431, 568/437
See application file for complete search history.

(56) References Cited

U.S. PATENT DOCUMENTS

| | | | | |
|---|---|---|---|---|
| 3,485,876 A | * | 12/1969 | van de Mond | 568/430 |
| 3,946,067 A | * | 3/1976 | Kwiatek et al. | 560/51 |
| 4,390,728 A | * | 6/1983 | Daniel | 568/431 |
| 6,495,726 B1 | * | 12/2002 | Kantam et al. | 568/431 |
| 6,743,952 B2 | * | 6/2004 | Kantham et al. | 568/431 |
| 7,189,882 B2 | * | 3/2007 | Chaudhari et al. | 568/431 |

OTHER PUBLICATIONS

Borgaonkar et al. Liquid Phase Oxidation of Toluene to Benzaldehyde by Air. Ind. Eng. Chem. Prod. Res. Dev. 1984, 23, pp. 455-458.*

* cited by examiner

*Primary Examiner*—Sikarl A Witherspoon
(74) *Attorney, Agent, or Firm*—Schweitzer Corman Gross & Bondell LLP

(57) ABSTRACT

The present invention provides a liquid phase oxidation of toluene by using catalyst containing manganese (Manganese II acetate) in presence of Lewis acid (Stannous (II) chloride) and a bromide promoter (NaBr), at a temperature of 120° C. and at a pressure of air in the range of 70-400 psig, in presence of carboxylic acid (acetic acid), as a solvent, to obtain high selectivity to benzaldehyde (76%). High activity was obtained with minimum byproducts such as benzoic acid, benzyl alcohol and benzyl acetate.

16 Claims, No Drawings

PROCESS FOR THE LIQUID PHASE OXIDATION OF TOLUENE TO BENZALDEHYDE

FIELD OF THE INVENTION

The present invention relates to an improved process for liquid phase oxidation of toluene to benzaldehyde. Particularly the invention relates to a process wherein toluene is oxidized to benzaldehyde with high-selectivity using lean oxygen in presence of a catalyst containing manganese, a Lewis acid and an organic or an inorganic halide, in presence of an organic acid, as a solvent, wherein the product benzaldehyde is separated by distillation. The manganese catalyst, Lewis acid and halide promoters are separated by solvent extraction or distillation of product and are reused for the oxidation process.

BACKGROUND OF THE INVENTION

Benzaldehyde is widely used in flavors such as almond and chery in various fragrances for soaps and toiletries, chemical intermediates in manufacture of dyes perfumes, pharmaceuticals and pesticides and photographic chemicals, as a solvent for oils, resins some cellulose ethers, cellulose acetate and nitrate.

Benzaldehyde is produced by the hydrolysis of the corresponding side chain halogenated toluene compounds such as benzyl chloride at a temperature range of 100°-200° C. at normal or higher pressures in the presence of an excess hydrochloric acid (U.S. Pat. No. 4,229,379). In U.S. Pat. No. 4,450,298 a process is described for the vapor phase catalytic hydrolysis of benzyl chloride to benzaldehyde using a catalyst comprising activated carbon treated with sulphuric acid or impregnated with a metal chloride such as iron (III) chloride or a metal sulphate such as cupric sulphate. A major disadvantage of these processes is the generation of large amount of effluent. The benzaldehyde produced by these routes does not meet food grade specifications.

Vapor phase or liquid phase oxidation of toluene by air or $O_2$ is environmentally benign and provided the desired selectivities to the market driven products. World patent WO 95/20560 discloses a liquid phase process for the manufacture of benzaldehyde by the oxidation of toluene in presence of oxygen in a temperature and pressure range of 120°-200° C. and 2-50 atm, respectively in the presence of a catalyst comprising cobalt or manganese as a metal ion and bromide as a promoter. 10% conversion of toluene and 45% selectivity to benzaldehyde is obtained. Borgaonkar et al, [I & EC Prod. Res. Dev., 23(3), 459 (1984)] have reported lower (10%) conversion of toluene and 90% yield of benzaldehyde by the use of cobalt acetate and either sodium bromide or paraldehyde as a promoter in presence of air.

A process for the vapor phase oxidation of toluene to benzaldehyde and benzoic acid using a catalyst containing a mixture of silver vanadate and lead vanadate or silver arsenate in presence of oxygen or ozone is described in U.S. Pat. No. 3,485,876. This catalyst system suppresses the formation of benzoic acid and degradation to carbon dioxide.

According to U.S. Pat. No. 3,946,067, aromatic aldehydes such as benzaldehyde or substituted benzaldehydes were manufactured by the vapour-phase oxidation of aralkyl compounds, like toluene or substituted toluenes, in the presence of catalyst containing palladium metal and phosphoric acid at a temperature of less than 250° C. The aromatic aldehydes are produced in a single reaction step. The drawbacks of the process are that the conversion of toluene has to be kept very low (<4%) for obtaining high selectivity (>70%). Also, the process is not suitable as large amounts of carbon dioxide are formed due to the high temperature used for the reaction. U.S. Pat. No. 4,390,728, describes a process in which the oxides of various metals (viz. Cu, Fe, Pb, U, Mo and P) with promoter were used for the production of benzaldehyde by the oxidation of toluene. At a temperature of 475°-550° C., a conversion of 35-50% and selectivity of 40-70% to benzaldehyde was obtained. U.S. Pat. No. 4,137,259 describes a process wherein silver vanadate and iron vanadate on silica is used as a catalyst at a temperature range 300°-500° C. in the presence of oxygen or ozone and steam. The conversion of toluene was found to be 21% and lower selectivity to aldehyde. A large amount of carbon oxide formation was observed in this process. U.S. Pat. No. 3,989,674, describes a process using Cu—Au silica catalyst system. In this process, a mixture of toluene, oxygen and helium in the molar ratio of 1:2:8 is passed over the catalyst at atmospheric pressure and temperature in the range of 230-390° C. The selectivity to benzaldehyde of 75-80% was obtained at a conversion level of only 15-30%. Another process for the production of benzaldehyde was reported by Ray et al. [Ind. J. Technol., 21(4), 137 (1983)] at a conversion of about 15% and selectivity of 70% with significant amount of $CO_2$ formation. Hence, the major disadvantages of the above processes are the use of high temperatures and lower conversion of toluene. The formation of large amount of carbon dioxide ultimately will affect the overall yield and is also not environmentally clean.

Thus, because of the above drawbacks these processes are not promising for the production of benzaldehyde by toluene oxidation.

Parteinheimer (J. Mol. Catal. 67, 35, 1991) has reported the use of HBr as a promoter in the cobalt catalyst system for the liquid phase oxidation of toluene. For this catalyst system, a very low yield for benzaldehyde (3%) and high yield of benzoic acid (91%) was obtained. In U.S. Pat. No. 6,495,726 a process is described for the production of benzaldehyde by liquid phase air oxidation of toluene using cobalt and manganese metal salts in the presence of zinc bromide as a promoter. The selectivity to benzaldehyde was reported to be 63% with toluene conversion of only 13%. Reference may be made to another U.S. Pat. No. 6,743,952, in which 40-50% benzaldehyde was obtained in liquid phase oxidation of toluene using a catalyst system comprising salts of iron, cobalt, manganese, molybdenum or nickel as catalyst, salts of manganese or copper as co-catalyst and cobalt bromide, sodium bromide, sodium chloride or zinc bromide as promoter. The invention used a catalyst, a co-catalyst and a promoter to achieve only 40-50% benzaldehyde. Moreover the process does not use any Lewis acid to increase the selectivity to benzaldehyde. The process used only metal bromide or chloride as promoter, where quaternary ammonium or phosphonium halides are not recommended.

OBJECTIVES OF THE INVENTION

The main objective of the present invention is to provide an improved process for liquid phase oxidation of toluene to benzaldehyde, which obviates the drawbacks as detailed above.

Yet another object of the present invention is to demonstrate the efficient and recyclable catalysts for toluene oxidation to benzaldehyde.

Yet another object of the present invention is to develop a process, which will be eco-friendly and avoids the effluent disposal problem.

Yet another object of this invention is to provide a toluene oxidation process, which uses a wide variety of oxygen source, preferably a cheap and readily available source such as air.

Yet another object of this invention is to reduce the formation of side products such as benzyl alcohol and benzoic acid.

These and other related objects of the present invention are achieved by providing an improved process for liquid phase oxidation of toluene to benzaldehyde wherein toluene is oxidized to benzaldehyde with high selectivity using lean oxygen in presence of a catalyst containing manganese, a Lewis acid and an organic or an inorganic halide in presence of an organic acid as a solvent, in which the product benzaldehyde can be separated by distillation, and the manganese catalyst, Lewis acid and halide promoters can be separated by solvent extraction or distillation of product and reused for the oxidation process.

SUMMARY OF THE INVENTION

Accordingly the present invention provides an improved process for the oxidation of toluene to benzaldehyde, which comprises reacting toluene with lean oxygen in presence of a composite catalyst system comprising a catalyst containing manganese, a Lewis acid and an organic or an inorganic halide, as promoter, in presence of an organic acid, as a solvent, at a temperature in the range of 50-150° C., at pressure in the range of 20-1000 psig, for a period of 3-5 hrs to obtained the desired product of benzaldehyde, separating the resultant benzaldehyde product either by distillation or solvent extraction and leaving behind the manganese catalyst, Lewis acid and halide promoters for being reused for another cycle of oxidation process.

In an embodiment of the present invention the catalyst containing manganese used is a salt of manganese selected from the group consisting of manganese acetate, manganese chloride, manganese bromide, manganese iodide, manganese nitrate, manganese carbonate, manganese sulfate, manganese oxide and manganese phosphate.

In yet another embodiment the Lewis acid promoter used is a carbonate, halide, acetate, phosphate, nitrate or sulphate salt of $Na^+$, $K^+$, $Be^{2+}$, $Mg^{2+}$, $Ca^{2+}$, $Al^{3+}$, $Sc^{3+}$, $In^{3+}$, $Ti^{4+}$, $Zr^{4+}$, $U^{4+}$, $Sn^{4+}$, $Sn^{2+}$, $Sb^{3+}$, $Bi^{3+}$, $Ir^{3+}$, $Ru^{2+}$, $Ag^+$, $Au^+$, $Tl^+$, $Hg^{2+}$, $Pd^{2+}$, $Cd^{2+}$, $Pt^{2+}$ or $Tl^{3+}$.

In yet another embodiment the inorganic halide promoter used is chloride, bromide or iodide salt, preferably a bromide salt of Li, Na, K, Cs, Be, Ca, Mg, Sr or Ba.

In yet another embodiment the organic halide promoter used is a compound having a general formula $R_1R_2R_3R_4NX$ or $R_1R_2R_3R_4PX$ wherein R1, $R_2$, $R_3$ and $R_4$ are same or different and are/is H or an alkyl group containing 1-5 carbon and X is a halogen atom selected from the group consisting of F, Cl, Br and I.

In yet another embodiment the molar ratio of manganese to Lewis acid promoter used is in the range of 0.1 to 10, preferably 0.3 to 0.6.

In yet another embodiment the molar ratio of manganese to inorganic or an organic halide promoter used is in the range of 0.1 to 10, preferably 0.1 to 0.2.

In yet another embodiment the molar ratio of manganese to toluene used is in the range of 0.1 to 10, preferably 0.3 to 5%.

In yet another embodiment the organic acid used as a solvent is a carboxylic acid selected from the group consisting of acetic acid, propionic acid, butanoic acid, pentanoic acid and benzoic acid.

In yet another embodiment the concentration of oxygen in gas phase used is in the range of 1-30% in an inert gas selected from nitrogen, helium and argon In yet another embodiment the lean oxygen used is compressed air.

In yet another embodiment the temperature used for the oxidation of toluene is in the range of 70-140° C.

In yet another embodiment the pressure of lean oxygen used is in the range of 70-400 psig.

In yet another embodiment the product benzaldehyde is separated from the reaction mixture by distillation.

In yet another embodiment the manganese catalyst, Lewis acid and organic or inorganic halide promoters used in the oxidation reaction are reused for further cycles of oxidation of toluene.

In still another embodiment the selectivity to benzaldehyde obtained is in the range of 50-76%.

The invention is described herein bellow with reference to the following examples, which are illustrated and should not be construed as limiting the scope of the invention in any manner.

EXAMPLE 1

| A 300 ml autoclave was charged with the following: | |
| --- | --- |
| Toluene: | 0.11 moles |
| Manganese (II) acetate: | 0.00054 moles |
| Aluminium (III) chloride: | 0.0011 moles |
| Sodium bromide: | 0.0011 moles |
| Acetic acid: | 50 ml. |

The autoclave was pressurized with air at room temperature to 250 psig and then heated to 120° C. for 4 hours and the reactor was maintained at 300 psig by filling the oxygen from the gas reservoir. The reaction was stopped after 4 hour; the reactor was cooled to room temperature and the gas mixture vented off. The liquid contents were analyzed by gas chromatography. The results of the gas chromatography showed 6% conversion of toluene and selectivity to benzaldehyde 73%, benzyl alcohol 2.3%, benzyl acetate 5% and benzoic acid 10%. The products were confirmed by GC-MS. The analysis of gas phase was carried out to using gas chromatography where no CO and $CO_2$ were found.

EXAMPLE 2

| A 300 ml autoclave was charged with the following: | |
| --- | --- |
| Toluene: | 0.11 moles |
| Manganese(II) acetate: | 0.0011 moles |
| Aluminium (III) chloride: | 0.0011 moles |
| Sodium bromide: | 0.0011 moles |
| Acetic acid: | 50 ml. |

The experimental procedure was same as described above in example 1. Manganese (II) acetate was charged 0.0011 moles instead of 0.00054 moles. The results of the gas chromatography showed 16% conversion of toluene and selectivity to benzaldehyde 60%, benzyl alcohol 2.6%, benzyl acetate 18% and benzoic acid 15%. The products were confirmed by GC-MS.

EXAMPLE 3

A 300 ml autoclave was charged with the following:

| | |
|---|---|
| Toluene: | 0.11 moles |
| Manganese (II) acetate: | 0.0011 moles |
| Aluminum (III) chloride: | 0.0011 moles |
| Sodium bromide: | 0.0011 moles |
| Acetic acid: | 50 ml. |

The experimental procedure was same as described above in example no-1. Three different reactions were carried out at different temperature; the result is given in Table 1.

| Tempeature (° C.) | Toluene conversion (%) | Selectivity (%) | | |
|---|---|---|---|---|
| | | PhCHO | PhCH$_2$OH | PhCOOH |
| 100 | 5 | 74 | 15.1 | 10.8 |
| 120 | 16 | 60 | 16.5 | 20.1 |
| 140 | 28 | 49 | 30.6 | 30.5 |

EXAMPLE 4

A 300 ml autoclave was charged with the following:

| | |
|---|---|
| Toluene: | 0.11 moles |
| Manganese (II) acetate: | 0.0011 moles |
| Tin (II) chloride: | 0.0011 moles |
| Sodium bromide: | 0.0011 moles |
| Acetic acid: | 50 ml. |

The experimental procedure was same as described above in Example no-1. The liquid contents were analyzed by gas chromatography. The results of the gas chromatography showed 10% conversion of toluene and selectivity to benzaldehyde 76%, benzyl alcohol 4.3%, benzyl acetate 7% and benzoic acid 12%. The products were confirmed by GC-MS.

EXAMPLE 5

A 300 ml autoclave was charged with the following:

| | |
|---|---|
| Toluene: | 0.11 moles |
| Manganese (II) acetate: | 0.0011 moles |
| Tin (II) chloride: | 0.0011 moles |
| Sodium bromide: | 0.0011 moles |
| Acetic acid: | 50 ml. |

The experimental procedure was same as described above in example no-1. The effect of pressure was studied at 500 and 700 psig. The results are shown in Table 2.

TABLE 2

| Pressure Psig | Toluene conversion (%) | Selectivity (%) | | |
|---|---|---|---|---|
| | | PhCHO | PhCH$_2$OH | PhCOOH |
| 500 | 19.3 | 66 | 15.0 | 18.8 |
| 700 | 21.9 | 60 | 16.5 | 23.3 |

EXAMPLE 6

A 300 ml autoclave was charged with the following:

| | |
|---|---|
| Toluene: | 0.11 moles |
| Manganese (II) acetate: | 0.0021 moles |
| Tin (II) chloride: | 0.0011 moles |
| Sodium bromide: | 0.0011 moles |
| Acetic acid: | 50 ml. |

The experimental procedure was same as described above in example no-1. The liquid contents were analyzed by gas chromatography. The results of the gas chromatography showed 18% conversion of toluene and selectivity to benzaldehyde 68%, benzyl alcohol 5.3%, benzyl acetate 10.2% and benzoic acid 17%. The products were confirmed by GC-MS.

EXAMPLE 7

A 300 ml autoclave was charged with the following:

| | |
|---|---|
| Toluene: | 0.11 moles |
| Manganese (II) acetate: | 0.0011 moles |
| Tin (IV) chloride: | 0.0011 moles |
| Sodium bromide: | 0.0011 moles |
| Acetic acid: | 50 ml. |

The experimental procedure was same as described above in example no-1. The liquid contents were analyzed by gas chromatography. The results of the gas chromatography showed 10% conversion of toluene and selectivity to benzaldehyde 60%, benzyl alcohol 7.3%, benzyl acetate 13.2% and benzoic acid 20%. The products were confirmed by GC-MS.

EXAMPLE 8

A 300 ml autoclave was charged with the following:

| | |
|---|---|
| Toluene: | 0.11 moles |
| Manganese (II) acetate: | 0.0011 moles |
| Tin (IV) chloride: | 0.0011 moles |
| Sodium bromide: | 0.0006 to 0.02 moles |
| Acetic acid: | 50 ml. |

The experimental procedure was same as described above in example no-1. The effect of bromide concentration on reaction was studied and tabulated in Table 4. The liquid and gas contents were analyzed by gas chromatography.

TABLE 4

| Sodium bromide (Moles) | Toluene conversion (%) | Selectivity (%) | | |
|---|---|---|---|---|
| | | PhCHO | PhCH$_2$OH | PhCOOH |
| 0.0006 | 5.6 | 58 | 20.1 | 22.5 |
| 0.02 | 19.2 | 54 | 13.8 | 30.6 |

EXAMPLE 9

| A 300 ml autoclave was charged with the following: | |
|---|---|
| Toluene: | 0.11 moles |
| Manganese (II) acetate: | 0.0011 moles |
| Antimony (III) chloride: | 0.0011 moles |
| Sodium bromide: | 0.0011 moles |
| Acetic acid: | 50 ml. |

The experimental procedure was same as described above in example no-1. The liquid contents were analyzed by gas chromatography. The results of the gas chromatography showed 15% conversion of toluene and selectivity to benzaldehyde 60%, benzyl alcohol 8.1%, benzyl acetate 16.2% and benzoic acid 17%. The products were confirmed by GC-MS.

EXAMPLE 10

| A 300 ml autoclave was charged with the following: | |
|---|---|
| Toluene: | 0.05 to 0.2 moles |
| Manganese (II) acetate: | 0.0011 moles |
| Antimony (III) chloride: | 0.0011 moles |
| Sodium bromide: | 0.0011 moles |
| Acetic acid: | 50 ml. |

The experimental procedure was same as described above in example no-1. The concentration of toluene was varied to study the effect of substrate concentration. The liquid and gas contents were analyzed by gas chromatography. The results are tabulated in Table 3.

TABLE 3

| Toluene (Moles) | Toluene conversion (%) | Selectivity (%) | | |
|---|---|---|---|---|
| | | PhCHO | PhCH$_2$OH | PhCOOH |
| 0.05 | 22.6 | 62 | 20.1 | 16.5 |
| 0.2 | 5.9 | 57 | 14.8 | 20.6 |

EXAMPLE 11

| A 300 ml autoclave was charged with the following: | |
|---|---|
| Toluene: | 0.11 moles |
| Manganese (II) acetate: | 0.0011 moles |
| Magnesium (II) chloride: | 0.0011 moles |
| Sodium bromide: | 0.0011 moles |
| Acetic acid: | 50 ml. |

The experimental procedure was same as described above in example no-1. The liquid contents were analyzed by gas chromatography. The results of the gas chromatography showed 17% conversion of toluene and selectivity to benzaldehyde 51%, benzyl alcohol 2.1%, benzyl acetate 4.2% and benzoic acid 42%. The products were confirmed by GC-MS.

The Main Advantages of the Present Invention Are:

1.1. The present invention provides an efficient method for liquid phase oxidation of toluene with cheaper catalysts at milder reaction conditions.
2. The present invention demonstrates recyclable catalysts for toluene oxidation.
3. The present process gives high conversion of toluene with high selectivity to benzaldehyde using Lewis acid promoters.
4. The process utilizes air as an oxidant, which is cheap and readily available, and can be carried at any composition of oxygen in an inert gas.
5. The process gives minimum byproducts such as benzoic acid, benzyl alcohol and benzyl acetate.

The invention claimed is:

1. An improved process for the oxidation of toluene to benzaldehyde, which comprises reacting toluene with lean oxygen in presence of a composite catalyst system comprising a catalyst containing manganese, a Lewis acid and an organic or an inorganic halide, as promoter, in presence of an organic acid, as a solvent, at a temperature in the range of 50-150° C., at pressure maintained in the range of 20-1000 psig, continued for a period of 3-5 hrs to obtain the desired product of benzaldehyde, separating the resultant benzaldehyde product either by distillation or solvent extraction and leaving behind the manganese catalyst, Lewis acid and halide promoters for being reused for another cycle of oxidation process.

2. An improved process according to claim 1, wherein the catalyst containing manganese used is a salt of manganese selected from the group consisting of manganese acetate, manganese chloride, manganese bromide, manganese iodide, manganese nitrate, manganese carbonate, manganese sulfate, manganese oxide and manganese phosphate.

3. An improved process according to claim 1, wherein the Lewis acid promoter used is a carbonate, halide, acetate, phosphate, nitrate or sulphate salt of $Na^+$, $K^+$, $Be^{2+}$, $Mg^{2+}$, $Ca^{2+}$, $Al^{3+}$, $Sc^{3+}$, $In^{3+}$, $Ti^{4+}$, $Zr^{4+}$, $U^{4+}$, $Sn^{4+}$, $Sn^{2+}$, $Sb^{3+}$, $Bi^{3+}$, $Ir^{3+}$, $Ru^{2+}$, $Ag^+$, $Au^+$, $Tl^+$, $Hg^{2+}$, $Pd^{2+}$, $Cd^{2+}$, $Pt^{2+}$ or $Tl^{3+}$.

4. An improved process according to claim 1, wherein the inorganic halide promoter used is chloride, bromide or iodide salt of Li, Na, K, Cs, Be, Ca, Mg, Sr or Ba.

5. An improved process for the oxidation of toluene to benzaldehyde, which comprises reacting toluene with lean oxygen in presence of a composite catalyst system comprising a catalyst containing manganese, a Lewis acid and an organic or an inorganic halide, as promoter, in presence of an organic acid, as a solvent, at a temperature in the range of 50-150° C., at pressure in the range of 20-1000 psig, for a period of 3-5 hrs to obtained the desired product of benzaldehyde, separating the resultant benzaldehyde product either by distillation or solvent extraction and leaving behind the manganese catalyst, Lewis acid and halide promoters for being reused for another cycle of oxidation process, and where the organic halide promoter used is a compound having a general formula $R_1R_2R_3R_4NX$ or $R_1R_2R_3R_4PX$ wherein $R1, R_2, R_3$ and $R_4$ are same or different and are/is H or an alkyl group containing 1-5 carbon and X is a halogen atom selected from the group consisting of F, Cl, Br and I.

6. An improved process according to claim 1, wherein the molar ratio of manganese to Lewis acid promoter used is in the range of 0.3 to 0.6.

7. An improved process according to claim 1, wherein the molar ratio of manganese to inorganic or an organic halide promoter used is in the range of 0.1 to 0.2.

8. An improved process according to claim 1, where the molar ratio of manganese to toluene used is in the range of 0.3 to 5%.

9. An improved process according to claim 1, wherein the organic acid used as a solvent is a carboxylic acid selected from the group consisting of acetic acid, propionic acid, butanoic acid, pentanoic acid and benzoic acid.

10. An improved process according to claim 1, wherein the concentration of oxygen in gas phase used is in the range of 1-30% in an inert gas selected from nitrogen, helium and argon.

11. An improved process according to claim 1, where the lean oxygen used is compressed air.

12. An improved process according to claim 1, wherein the temperature used for the oxidation of toluene is in the range of 70-140° C.

13. An improved process according to claim 1, wherein the pressure of lean oxygen used is in the range of 70-400 psig.

14. An improved process according to claim 1, wherein the product benzaldehyde is separated from the reaction mixture by distillation.

15. An improved process according to claim 1, wherein the manganese catalyst, Lewis acid and organic or inorganic halide promoters used in the oxidation reaction are reused for further cycles of oxidation of toluene.

16. An improved process according to claim 1, where the selectivity to benzaldehyde obtained is in the range of 50-76%.

* * * * *